United States Patent [19]

Ballerini et al.

[11] Patent Number: 4,904,586

[45] Date of Patent: Feb. 27, 1990

[54] ENZYMATIC PROCESS FOR TREATING XANTHAN GUMS IN ORDER TO IMPROVE THE FILTERABILITY OF THEIR AQUEOUS SOLUTIONS

[75] Inventors: Daniel Ballerini, Saint Germain en Laye; Yves Benoit, Ermont; Frédéric Monot, Le Mesnil le Roi, all of France

[73] Assignee: Institut Francais du Petrole, Rueil-Malmaison, France

[21] Appl. No.: 46,223

[22] Filed: May 5, 1987

[51] Int. Cl.$^4$ .................. C12P 19/06; C12P 39/00; C13L 3/00; E21B 43/22

[52] U.S. Cl. ........................ 435/114; 435/42; 435/274; 166/246

[58] Field of Search ............. 166/246; 435/42, 104, 435/274–276, 817

[56] References Cited

U.S. PATENT DOCUMENTS

| | | | |
|---|---|---|---|
| 3,966,618 | 6/1976 | Colegrove | 166/246 |
| 4,119,491 | 10/1978 | Wellington | 210/606 |
| 4,165,257 | 8/1979 | Stokke | 166/246 |
| 4,299,825 | 11/1981 | Lee | 514/54 |
| 4,326,037 | 4/1982 | Griffith et al. | 166/246 |
| 4,412,925 | 11/1983 | Ballerini et al. | 166/246 |
| 4,416,990 | 4/1983 | Rinaudo et al. | 435/104 |
| 4,431,734 | 2/1984 | Rinaudo et al. | 435/42 |

*Primary Examiner*—Barry S. Richman
*Assistant Examiner*—William H. Beisner
*Attorney, Agent, or Firm*—Millen, White & Zelano

[57] ABSTRACT

Process for treating a xanthan gum in order to improve the filterability of its aqueous solutions, comprising an enzymatic treatment of an aqueous solution of xanthan gum containing, as dissolved salts, a proportion of alkali and/or alkaline-earth metals of at least $10^{-2}$ equivalent/liter, said treatment being performed by means of two enzyme extracts of different types, a so-called PG enzyme having as main activity a polygalacturonase activity and a so-called P enzyme extract whose main activity is a protease activity, in conditions compatible with the activity of said enzyme extracts. The obtained xanthan gum powder or solution can be used as enhanced oil recovery agent.

9 Claims, No Drawings

ENZYMATIC PROCESS FOR TREATING XANTHAN GUMS IN ORDER TO IMPROVE THE FILTERABILITY OF THEIR AQUEOUS SOLUTIONS

This invention has for object an improvement in the process according to U.S. Pat. No. 4 431 734.

BACKGROUND OF THE INVENTION

U.S. Pat. No. 4 431 734 discloses an enzymatic process for treating xanthan gums in order to improve the filterability and the capacity of xanthan gum aqueous solutions to be injected into and circulate through oil formations, so as to enhance the crude oil recovery. This process comprises a suitable treatment with two enzyme systems, the first of polysaccharase type in acid or substantially neutral pH, the second of protease type in basic, neutral or acid pH, and provides for an improvement of the injectivity and flowing properties of xanthan solutions through the oil formations without loss of the intrinsic properties and particularly of the thickening power of the polysaccharide.

According to this patent the enzymatic treatments by means of an enzyme of polysaccharase type and of an enzyme of protease type may be performed either simultaneously at a pH compatible with a sufficient activity of both enzymes or successively at a pH suitable for the type of enzyme selected in each step. The best results are obtained with an operation in two successive steps, the first step being performed with polysaccharase and then the second step with protease.

The enzyme extracts called polysaccharases, usually obtained by aerobic cultivation of fungi pertaining to the category of Basidiomycetes or fungi pertaining for example to the Aspergillus, Fusarium, Myrothecium, Penicillium, Polyporus, Rhizopus, Sclerotinia, Sporotrichum and Trichoderma genera can be used in the process of this patent.

These enzymes, liable to hydrolyze polysaccharides, are usually sold in the trade under the name of cellulases and are used in the process according to this patent under pH, temperature and salt concentration conditions such that the characteristics of the xanthan gum itself is not substantially modified.

The second category of enzyme extracts to be used complementarily to the preceding category in the process according to this patent is formed by the category of bacterial proteases. These proteases are generally produced by microorganisms of the Bacillus genus such as B. Subtilis, B. licheniformis, B. amyloliquefaciens and B. pumilis, or still of Streptomyces genus such as S. fradiae, S. griseus and S. rectis. The enzyme source is however not critical. These proteases are called acid, neutral or alkaline proteases when their acitivity is optimum respectively at slightly acid, neutral or basic pH values.

The enzymatic treatment according to this process is preferably performed during a total incubation period of 0.5–60 hours, preferably 4–48 hours, at temperatures ranging from room temperature (about 25° C.) up to about 65° C., preferably at 40°–60° C. Short treatment periods are preferably associated with high temperatures and conversely.

The enzymatic treatments are performed in aqueous medium wherein the alkali and/or alkaline-earth metals are dissolved in a proportion of at least $10^{-2}$ equivalent/liter, preferably at least $10^{-1}$ equivalent/liter. The relative synergism effect obtained by this process is however the more substantial as the salt content of the treatment water is higher. A particular aspect of the process according to this patent consists in the fact that the synergism activity of the two enzyme preparations is also obtained in the presence of divalent ions, e.g. $Ca^{++}$ or $Mg^{++}$, particularly the field water.

OBJECTS OF THE INVENTION

A first object of the present invention is to provide an improved method to clarify aqueous solutions of xanthan gums, wherein the thickening power of said gums is maintained. Another object of the invention consists in improving the clarification of the fermentation liquor as well as of the aqueous dispersions of xanthan gums available as powder. Another object of the invention consists of removing the insoluble cell fragments resulting from the fermentation of these xanthan gums. Another object of the invention consists in improving the injectivity of the xanthan gum solutions for use in enhanced oil recovery. Still another object of the invention consists in removing microgels and hence improving the flowing properties of the xanthan gum solutions inside an oil formation at a certain distance from the injection well. Finally, another object of the invention consists in using solid compositions for improving the limpidity, the injectivity and flowing properties of xanthan gum solutions.

SUMMARY OF THE INVENTION

The purpose of the present invention is to substitute other enzyme preparations or extracts for the first category of enzyme extracts used in the process according to U.S. Pat. No. 4 431 734.

According to the present invention an enzyme extract whose main activity is a polygalacturonase activity is used instead of an enzyme preparation of the polysaccharase type, also called cellulase, whose main enzymatic activity is a cellulolytic activity. Thus, according to the present invention, two enzyme extracts of different types are used, a so-called PG enzyme extract as hereinafter defined and a so-called P extract as hereinafter defined, in conditions compatible with the activity of said enzyme extracts.

The enzyme extracts used according to the invention have generally several other activities. However it is essential that for PG extract the polygalacturonase activity be the main activity, the other activities, for example cellulase, acid protease, xylanase etc. ... being only secondary. The considered PG extracts have generally only a small and preferably no substantial cellulase activity. Preferably an enzyme extract having a polygalacturonase activity of endo type will be used.

By main activity it is meant a generally major activity among the numerous activities of the enzyme extract. The enhancement of this activity is generally favored by selection of the culture medium and of the strain of producing microorganism when the enzyme extract originates from microbes or fungi. Enzymes may also be separated so as to obtain an increased content and purity adapted to a desired activity.

With respect to the enzymes used according to U.S. Pat. No. 4 431 734, the polysaccharase obtained by cultivation of Basidiomycete of Poria genus, as recommended in this patent, has a main activity of cellulase type of about 50 000 Carboxymethylcellulase (CMCase) units per gram of preparation, i.e. about 250 units per mg of proteins.

The CMCase activity measuring the cellulase activity of an enzyme extract corresponds to the number of glucose micromoles released from carboxymethylcellulose, the test being conducted for 30 minutes at a pH of 4.6 and at 37° C. In order to make comparable the enzymatic activities of preparations in powder and in liquid form, it is preferred to use the specific activities (per mg of proteins).

The polygalacturonase activity of an enzyme extract corresponds to the number of galacturonic acid micromoles released from polygalacturonic acid, the test being conducted for 30 minutes at a pH of 4.0 and at 40° C.

In the above-mentioned U.S. patent the polygalacturonase activity of the polysaccharase, sold in the trade under the name of cellulase, obtained from Basidiomycete of Poria genus, is of about 5 units per mg of proteins.

The enzymatic activities of polygalacturonase type are usually produced by cultures of bacteria of Erwinia or Pseudomonas genus, of yeasts of Kluyveromyces genus or of fungi of Aspergillus, Rhizopus, Fusarium, Rhizoctonia, Penicillium, Sclerotinia and Verticillium genera.

From a strain of microorganism, for example *Aspergillus niger,* it is possible to obtain enzyme abstracts whose main enzymatic activity is either of the cellulase type (polysaccharase) or of the polygalacturonase type. The selection of the carbon source for the culture medium has a substantial effect on the capacity of the microorganism to produce mainly a determined enzymatic activity. Thus for obtaining polygalacturonase as main activity, it is often necessary to use as carbon source a carbon hydrate containing pectine (pectine of the trade, wheat-bran, beet pulps . . . ). The medium may further contain sources of mineral salts and nitrogen. After culture for example at 30° C. for a few days, the medium is freed from the cells by filtration or centrifugation and may be used as enzyme extract having a main polygalacturonase activity. The protein content of the extract may then be increased for example by ultrafiltration or by precipitation of proteins by means of solvents (e.g. acetone, ethanol) or salts (e.g. ammonium sulfate).

The enzyme extracts used according to the invention have only a low cellulase activity. Examples of industrial preparations are in particular enzyme extracts called pectinases obtained from a culture of a fungus of Aspergillus genus and more particularly from *Aspergillus Niger.*

The protease activity of the enzyme extracts of PG type, measured in ANSON units per gram of enzyme extract as hereinafter described, is usually lower than 0.05 unit and preferably lower than 0.01 and more advantageously lower than 0.005 unit. When measuring the specific enzymatic activities of extracts in units per milligram of proteins, "C" being the cellulase activity and "PG" the polygalacturonase activity of these extracts, the enzyme extracts preferably used according to the invention are those whose C/PG ratio is lower than 1, preferably lower than 0.5 and more preferably lower than 0.1.

Thus, according to the present invention, the filterability of xanthan gum aqueous solutions is improved by treating said solutions with an enzyme extract whose main activity is a polygalacturonase activity (PG extract) and with an enzyme extract whose main activity is a protease activity (said extract will be called P extract) in conditions compatible with the activity of said extracts.

The protease activity may be determined by the KUNITZ method. Then, 1 protease unit corresponds to the amount of enzyme extract releasing an amount of substances not precipitable with TCA (trichloroacetic acid) having an optical density at 550 nm equivalent to the optical density given by 0.4 g of tyrosine with the FOLIN reactant. The temperature of the test is 37° C. and the reaction time 20 minutes. When alkaline or neutral proteases are concerned, the substrate is 1% casein and, when acid proteases are concerned, the substrate is 1% bovine serumalbumin. The pH values at which are measured the alkaline, neutral and acid protease activities are respectively 10, 7 and 3.

Other protease units are used as the ANSON unit which is the enzyme amount which, under standard conditions (25° C. ; pH of 7.5 ; 10 minutes), digests hemoglobine at such initial velocity that it releases per minute an amount of products soluble in TCA which gives the same coloration with the phenol reactant as a milliequivalent of tyrosine.

Thus, for example, 0.6 L ALCALASE (trade mark of Novo Industrie A/S) is a liquid preparation obtained by fermentation of *Bacillus licheniformis* which contains as main activity (protease) 0.6 ANSON unit per gram and no substantial other enzymatic activity.

Generally enzyme extracts obtained from bacteria of Bacillus genus, whose main activity is the protease activity, do not substantially contain polygalacturonase or cellulase activities as secondary activities.

Usually enzyme extracts whose main activity is the protease activity used according to the present invention, have polygalacturonase and cellulase activities, expressed in units per milligram of proteins, respectively lower than 5, preferably lower than 1 and often advantageously lower than 0.5.

The enzyme extracts whose main activity is a protease activity have an activity, measured in ANSON units per gram of enzyme extract, usually of at least 0.1 unit and preferably from 0.2 to 10 units.

One of the other interesting features of the present invention is the incorporation with the solution of polysaccharides of only small amounts of proteins by selecting an enzyme preparation particularly active for removing plugging agents present within the polymer solutions. When using an enzyme preparation such as that disclosed in U.S. Pat. No. 4 431 734, whose main activity is the cellulase activity and containing polygalacturonase activity as one of the secondary activities, it is necessary to add relatively high amounts of enzymes (hence proteins). For example for the cellulase obtained from Basidiomycete of Poria genus, according to example 1 of this patent, about 30% by weight of enzyme in proportion to the polysaccharide are introduced.

Now, it has been observed that proteins may act as plugging agent in polysaccharide solutions when they are used in a too high amount. Consequently it is highly preferable to add the lowest possible protein amount when the treatment has for object to improve the filterability of polysaccharide solutions. It is hence judicious to use an enzyme preparation acting mainly on the aggregates, so that the proportion of active substance (hence proteins) to introduce for having an effieient treatment can be decreased. It has been surprisingly discovered that so-called PG enzyme extracts provide for a strong improvement of the filterability of xanthan solutions, particularly when the treatment by an enzyme extract having said activity is associated with a treatment by a so-called P enzyme extract of the bacterial protease category. Then, by using both treatments, it is possible to clarify polysaccharide solutions with small amounts of proteins, clearly lower than those used according to U.S. Pat. No. 4 431 734.

The enzymatic treatment according to the present invention may be performed either in the simultaneous presence of a PG extract and of a P enzyme extract at a pH value compatible with a sufficient level of both activities, or successively by means of a first enzyme extract of one of the two above-mentioned types at a suitable pH for the selected type and then of an enzyme extract of the other type at a suitable pH for said other type, for example the PG extract at an acid pH followed with the P extract at a slightly acid, neutral or basic pH according to the type of P extract, or the contrary. The best results are obtained when proceeding in two successive steps, first with the PG extract, then with the P extract.

The enzymatic treatment of the invention is performed in aqueous medium wherein are dissolved alkali and/or alkaline-earth metals at a concentration of at least $10^{-2}$ equivalent/liter, preferably at least $10^{-1}$ equivalent/liter. The obtained relative synergism effect is relatively insensitive to the salt content. Although salt contents higher than about 1 equivalent/liter might be used, it is generally preferred to use salt contents ranging from at least $10^{-2}$ equivalent/liter to at most 1 equivalent/liter. A particular aspect of the present invention consists in that the synergism activity of both enzyme types is also obtained in the presence of divalent ions, for example $Ca^{++}$ or $Mg^{++}$, particularly of the field water.

The simultaneous or successive enzymatic treatments according to the invention preferably take place during an incubation period lasting a total of 0.5-60 hours, preferably 4-48 h, at temperatures ranging from about 15° C. to about 70° C., preferably from 20° to 60° C. Short treatment times are preferably associated with high temperatures and conversely. When performing the enzymatic treatment at the highest temperatures, the optimum time will be relatively short, for example 2-24 h at 50° C., 1-12 hours at 60° C. Preferred temperatures range from 20° to 60° C. and will preferably not exceed 70° C. since at said temperature the enzyme extracts are liable to deactivate substantially.

PG extracts are used in the process conforming with the invention under conditions of pH ($3 < pH < 7$), of temperature (15°-70° C.) and of salt concentration ($>10^{-2}$ equivalent/liter) as above indicated, such that the properties of the xanthan gum be not substantially modified.

The other category of enzyme extracts used according to the invention is formed of the extracts of the bacterial protease category. These P extracts are usually produced by microorganisms of Bacillus genus such as *B. subtilis*, *B. licheniformis*, *B. amyloliquefaciens* and *B. pumilis* or still of the Streptomyces genus such as *S. fradiae*, *S. griseus* and *S. rectis*. The extract source is however not critical. The optimum activity of these P extracts may be obtained either at slightly acid or neutral or basic pH values. They are then respectively called acid, neutral or alkaline P extracts. Of course, when a simultaneous treatment with a PG extract and a P extract is performed, the selected enzyme species will be those whose range of activity, as far as pH is concerned, will overlap.

Although the synergism treatment according to the present invention applies essentially to dispersions in salted water of xanthan gums as powder, it is also obviously applicable to fermentation broths. Moreover, xanthan gums separated from a so-treated fermentation broth no longer require any further enzymatic treatment and the filterability of their aqueous solutions is considerably improved. The techniques for separating a xanthan gum is powder from a fermentation broth are well-known in the art and consist for example in a precipitation with an alcohol miscible to the fermentation broth or still in a drying process by lyophilization or solvent evaporation.

The synergism process of the present invention, using simultaneous or successive treatments with a PG extract and a P extract, first provides for a degradation of solid cell and bacteria fragments suspended in the xanthan gum solutions by converting them to hydrosoluble compounds so as to finally obtain a limpid solution. Moreover, and this is the more surprising, this synergism treatment makes it possible to remove translucent microgels responsible for the plugging of oil formations at a certain distance from the injection well. During this whole operation of clarification and microgel removal, the thickening power of the xanthan gum is kept and the obtained limpid solutions may then, after mere dilution and without further filtration treatment, be injected in the oil formations. The injectivity and flowing properties of said solutions through said formations are clearly improved as compared with those obtained by the treatments with enzyme extracts considered separately as it can be easily shown from the corresponding tests through calibrated filters.

In order to perform the simultaneous synergism treatment according to the process of the invention, starting from dispersions in an aqueous phase having the above-mentioned required salt content, of xanthan gums as powder, or from dilutions in the same aqueous phase of raw fermentation broth, the procedure may be as follows: if necessary the pH of the solution is adjusted to the pH value corresponding to the optimum activity of both types of enzyme extracts and these two enzyme extracts are added. The temperature is maintained in the range of 15°-70° C. for variable times in order to obtain the above-described filterability improvement. When necessary the pH of the solution is readjusted to the value of the pH of use and, after dilution to the desired concentration and viscosity, the so-treated solution is ready for use.

When it is desired to perform the enzymatic treatment according to the invention in two steps, the operation may be conducted as follows: if necessary the pH of the xanthan gum solution is brought to a value lower than 7 and higher than 3, advantageously from 3 to 6, by means for example of hydrochloric acid, acetic acid or sulfuric acid. The PG extract is added and the temperature maintained at 15°-70° C. for the required time as above-defined. The pH of the solution is then brought back, by means of a base, for example sodium or potassium hydroxide, to a value higher than 6 and lower than 12, advantageously from 6.5 to 9. After addition of the P extract, the temperature is again maintained at 15°-70° C. for the required time, as above-defined. After having readjusted the pH of the solution to the pH value of use and after dilution to the desired concentration and viscosity, the so-treated solution is ready for use.

An alternative embodiment of enzymatic treatment in two steps consists of first adjusting the pH of the solution to a value preferably ranging from 6.5 to 9 and performing the enzymatic treatment with P extract before readjusting the pH to slightly acid values, preferably from 3 to 6 and performing the enzymatic treatment with PG extract.

During the enzymatic treatment according to the invention, the proportion of xanthan gum is for example from 0.01 to 4%, preferably from 0.04 to 1.5% by weight with respect to water and the proportion of each enzyme extract is for example from 0.01 to 10% by weight of proteins, preferably from 0.025 to 5% by weight of proteins with respect to the xanthan weight, these proportions being not limitative. The minimum amount of enzyme extracts to be used obviously depends on the amount of active factor (hence of the polygalacturonase and protease activity) in the selected enzyme preparations.

According to an additional aspect of the present invention the solid composition containing xanthan gum and the two types of enzyme extracts may be directly added to the field water, thus avoiding any required separate addition of enzyme extracts to the xanthan gum solution when the simultaneous enzymatic treatment is contemplated. These solid compositions are of particular interest when the enzymatic clarification must be achieved, for example, on the mere site of the enhanced oil recovery operation. The enzymatic reaction will develop progressively as polysaccharide is dissolved and, by suitable selection of the temperature and of the pH of the dissolving water, the enzymatic treatment will not extend the usual time required for the preparation of the injected xanthan gum solution. It is thus possible to directly obtain a limpid solution having the desired viscosity and which may be directly used without any complementary treatment, particularly filtration treatment, and which has clearly improved injectivity and filterability properties for use in enhanced oil recovery operations.

Such a solid composition may contain for example from 10 to 100 000, preferably from 20 to 40 000 parts by weight of xanthan gum per part by weight of proteins of the mixture of enzyme extracts.

EXAMPLES

The following examples illustrate the invention and must not be considered as limiting the scope thereof.

EXAMPLE 1 (comparative)

This example concerns an enzymatic treatment involving a polysaccharase produced by Basidiomycete of Poria genus having a cellulase activity as main activity (25.000 CMCase units/l, i.e. 250 CMCase U/mg of protein) and a small polygalacturonase activity (500 polygalacturonase units/l, i. e. 5 U/protein mg) as one of its numerous secondary activities.

A 10 g/l solution of powdery polysaccharide Rhodopol 23 (Rhône Poulenc Industries—France), prepared in water containing 1 g/l of NaCl and 0.4 g/l of sodium azide as bacteriostatic agent, is used. After stirring for a few hours, the pH of the solution is adjusted to 4.5 and the temperature brought to 50° C. Then 500 mg/l of a polysaccharase enzyme preparation obtained from Basidiomycete of Poria genus are added and maintained in action for 16 hours. The introduced enzyme amount corresponds to the incorporation of 100 mg/l of proteins (1% by weight of proteins in proportion to xanthan).

The pH is then adjusted to 9.0 with 1 N sodium hydroxide and 500 mg/l of Alcalase (trade mark of Novo Industrie A/S), originating from a culture of Bacillus licheniformis having a protease activity of 0.6 ANSON unit per gram, are added. This enzyme extract has an alkaline protease activity as main activity and has practically no polygalacturonase or cellulase activity ; these activities are lower than $10^{-2}$ unit per milligram of protein. The treatment is discontinued after 6 hours of action of said enzyme extract at 50° C.

The samples withdrawn before enzyme addition, after action of the polysaccharase and after action of the Alcalase, are subjected to the quick filterability test disclosed in the main patent, in order to estimate the efficiency of the enzymatic treatment. This test consists of passing the obtained solutions, after dilution to a xanthan concentration of 0.4 g/l by means of water containing 1 g/l of NaCl and 0.4 g/l of $NaN_3$ and after adjustment of their pH to a value of 7, through a 0.8 nm Millipore filter ($\phi=47$ mm) under constant pressure of 10 kPa. The accumulated volume of filtrate is recorded during the filtration time. The results are reported in table 1 hereinafter.

TABLE 1

| $N_o$ | Solution | Filtrate volume accumulated in 20 minutes |
|---|---|---|
| 1 | Before treatment | 30 ml |
| 2 | After 16 hours of polysaccharase action | 160 ml |
| 3 | After 22 hours of polysaccharase action | 200 ml |
| 4 | After 16 h (polysaccharase) then 6 h (Alcalase) | 670 ml |

These results show the efficiency of the combined polysaccharase-Novo Alcalase treatment of the filterability of the xanthan solutions and the substantial synergism effect between the two enzyme preparations. The relative viscosity of the solutions is not substantially modified by the treatment.

EXAMPLE 2 (comparative)

The treatment described in this example has been conducted under conditions strictly identical to those of treatment n° 3 of example 1, except that the added polysaccharase amount is only 125 mg/l instead of 500 mg/l in the preceding example (i.e. 0.25% by weight of proteins in proportion to the xanthan weight). The introduced cellulase and polygalacturonase activities are respectively of 6250 CMCase units/l and of 125 Polygalacturonase units/l instead of 25 000 CMCase units/l and 500 polygalacturonase U/l in example 1.

Here, the efficiency of the combined polysaccarase-Novo Alcalase treatment is lower since the accumulated volume of filtrate, after combined action of polysaccharase and Novo Alcalase, is 300 ml in 20 minutes (instead of 670 ml in example 1).

EXAMPLE 3 (comparative)

The object of this example is to show the action of an enzyme containing, as precedingly, the cellulase activity as main activity, but whose polygalacturonase activity is still lower than that used in example 1.

This treatment has been performed under conditions similar to those of test n°4 of example 1: same initial solution, identical action of Novo Alcalase (however 2 periods have been tested : 2 h and 6 h), quick filterrability test.

The first enzyme to be used is an enzyme preparation (as lyophilized extract) produced by Trichoderma reesel and having a high cellulase activity (200 U/protein mg) and a very small polygalacturonase activity (1 U/protein mg). The protein content of said lyophilized extract is about 100 % and this extract is added, in proportion of 100 mg/l of protein, to the 10 g/l solution of Rhodopol 23 (identical to that of example 1) brought back to a pH of 4.8 at 50° C., conditions which are optimum for the enzyme action. Before addition of the P extract (Novo Alcalase) the cellulase action is maintained for 16 hours.

The results of the quick filterability tests are reported in table 2.

TABLE 2

| $N_o$ | Solution | Filtrate volume accumulated in 20 minutes |
|---|---|---|
| 1 | Before treatment | 30 ml |
| 2 | After 16 hours (cellulase) | 120 ml |
| 3 | After 16 h (cellulase) + 2 h (Alcalase) | 310 ml |
| 4 | After 16 h (cellulase) + 6 h (Alcalase) | 310 ml |

The relative viscosity of the solutions is not substantially changed by the action of these enzymatic preparations.

The final filterability is lower than that obtained in example 1. This enzymatic preparation, whose polygalacturonase activity is low, is not well adapted to the removal of the plugging agents present in the polysaccharide solution. This example shows in particular that the cellulase activity is not the main activity responsible for the the filterability improvement.

EXAMPLE 4

An enzymatic preparation obtained from an *Aspergillus niger* culture is used in this example. This extract, called PG extract, has a polygalacturonase activity as main activity.

The treatment is performed in conditions similar to those of the preceding examples, i.e.: preparation of a 10 g/l Rhodopol 23 solution in water containing 1 g/l of NaCl and 0.4 g/l of $NaN_3$, action of the PG extract obtained from *Aspergillus niger* at pH 4.0 and 40° C. for 16 hours, followed by the action of Novo Alcalase of *Bacillus licheniformis* at pH 9.0 and 50° C. for 2 h or 6 h.

The PG extract is added so as to introduce 100 mg/l of proteins. This enzyme contains only a small amount of CMCase, about 1 unit per mg of protein and about 60 polygalacturonase units per mg of protein, which constitutes the main activity, the protease activity being lower than 0.01 ANSON unit per enzyme gram.

The withdrawn solutions are diluted to 0.4 g/l of polymer and subjected to the quick filterability test. The results are reported in table 3 and the relative viscosities do not substantially change during the treatment.

TABLE 3

| $N_o$ | Solution | Filtrate volume accumulated in 20 minutes |
|---|---|---|
| 1 | Before treatment | 30 ml |
| 2 | After 16 h (PG extract) | 210 ml |
| 3 | After 18 h (PG extract) | 220 ml |
| 4 | After 22 h (PG extract) | 230 ml |
| 5 | After 16 h (PG extract) + 2 h (Alcalase) | 750 ml |
| 6 | After 16 h (PG extract) + 6 h (Alcalase) | 820 ml |

TABLE 3-continued

| $N_o$ | Solution | Filtrate volume accumulated in 20 minutes |
|---|---|---|
|  | 6 h (Alcalase) |  |

The results show that the first enzyme is perfectly adapted to the removal of the plugging agents of the polysaccharide solution and that the synergism effect with Alcalase is remarkable. Consequently, the replacement of an enzyme having a cellulase activity as main activity and a polygalacturonase activity as secondary activity by an enzyme having a low cellulase activity and polygalacturonase activity as main activity is highly recommended for improving the filterability of the xanthan solutions.

EXAMPLE 5 (comparative)

The treatment described in this example has been conducted under conditions identical to those of test n° 6 of example 4. The involved enzymatic preparation is also obtained from a culture of *Aspergillus niger* but its specific polygalacturonase activity is of 0.8 unit per mg of protein and its specific CMCase activity is of about 100 units per mg of protein. The protein introduced for the xanthan treatment amounts to 100 mg per liter of solution. The final filterability of the solution is of 200 ml in 20 minutes. Thus, although originating from the culture of the same microorganism as that of example 4, this enzyme extract is not much efficient for improving the filterability of polysaccharide solutions.

EXAMPLE 6

This example has for object to show the efficiency of an enzyme preparation having a very high polygalacturonase activity as a result of a partial purification.

The treatment conditions are similar to those of example 4, except for the first enzyme extract used. The latter is a partially purified PG extract originating from a culture of *Aspergillus niger*. Its polygalacturonase activity is about 120 units per mg of protein and its CMCase activity of about 10 units/protein mg. This enzyme extract is incorporated in a proportion of 5.6 mg protein/l (instead of 100 mg/l in the preceding examples). Here, the protein ratio by weight of PG extract/xanthan is about 0.056%. As compared with example 1, the introduced CMCase proportion is about 450 times lower, whereas the polygalacturonase proportion is about the same (670 units/l instead 500). This purified PG extract is allowed to act at 40° C. and pH 4 for 16 hours before addition of Novo Alcalase. Samples are subjected to the quick filterability test. The results are reported in table 4.

TABLE 4

| Solution | Filtrate volume accumulated in 20 minutes |
|---|---|
| Before treatment | 30 ml |
| After 16 h action of the purified PG extract | 130 ml |
| After 22 h action of the purified PG extract | 150 ml |
| After 16 h (purified PG extract) + 6 h (Alcalase) | 640 ml |

It has further been ascertained that the relative viscosity is substantially constant all along the enzymatic treatment.

This example shows that, by using a partially purified PG extract, a very substantial improvement of the filterability of xanthan solutions can be achieved with a very low amount of enzyme, hence of proteins. The cellulase amount incorporated with the partially purified PG extract is negligible, thus showing that the cellulolytic activity is not necessary for the clarification of polysaccharide solutions.

This example also shows the high synergism between the action of the PG extract and that of the P extract (alkaline protease : Novo Alcalase), thus providing a result substantially equivalent to that obtained in the above comparative example 1 with a clearly lower protein proportion (about 18 times less) which is particularly interesting and avoids any plugging risk due to a too high protein amount.

The xanthan gum aqueous solutions, made limpid by the enzymatic treatment according to the present invention, may be used directly, optionally after dilution at the desired concentration, without, without further treatment, as scavenging fluid in oil formations.

What is claimed as the invention is:

1. A process of improving the filterability of an aqueous xanthan gum solution containing at least $10^{-2}$ equivalent/liter of a salt selected from the group consisting of alkali metal salts, alkaline earth-metal salts and mixtures thereof, comprising contacting said solution with an enzyme extract exhibiting predominately polygalacturonase activity and an enzyme extract exhibiting predominately protease activity to enzymatically treat said aqueous xanthan gum solution.

2. A process according to claim 12, wherein both enzyme extracts of different types are simultaneously used in such conditions that these extracts of both types are simultaneously active.

3. A process according to claim 12, wherein the enzymatic treatment is performed in two successive steps, first with an enzyme extract of one type, then with an enzyme extract of the other type, the conditions of each step being so selected that the selected type of extract is active in this step.

4. A process according to claim 3, wherein the first step comprises the treatment with a PG extract and the second step the treatment with a P extract.

5. A process according to claim 4, wherein the first step is conducted with a PG extract at a pH from 3 to 7 and the second step with a P extract at a pH from 6 to 12, these two steps lasting, as a whole, from 0.5 to 60 hours and the temperature being from 15° to 70° C.

6. A process according to claim 12, wherein the PG extract is obtained from the culture of a fungus pertaining to the Aspergillus genus type and the P extract is obtained from the culture of a microorganism of Bacillus type.

7. A process according to claim 12, wherein the PG extract is obtained from a culture of *Aspergillus niger*.

8. A process according to claim 12, wherein the PG extract has a main polygalacturonase activity and a secondary activity of cellulase type (C) such that the C/PG activities ratio is lower than 1 and the protease activity lower than 0.05 ANSON unit per gram of PG extract, and the P extract has a main protease activity of at least 0.1 ANSON unit per gram of P extract and has cellulase and polygalacturonase activities lower than 5 units per milligram of proteins.

9. A process according to claim 12, wherein the extracts are used in such amounts by weight that the proportion of each of the PG and P extracts respectively represents a protein weight from 0.01 to 10% of the xanthan gum weight.

* * * * *